United States Patent
Chen et al.

(10) Patent No.: US 10,932,859 B2
(45) Date of Patent: Mar. 2, 2021

(54) IMPLANT SURFACE MAPPING AND UNWRAPPING METHOD

(71) Applicants: China Medical University, Taichung (TW); China Medical University Hospital, Taichung (TW)

(72) Inventors: Yi-Wen Chen, Taichung (TW); Cheng-Ting Shih, Taichung (TW)

(73) Assignees: China Medical University, Taichung (TW); China Medical University Hospital, Taichung (TW)

( * ) Notice: Subject to any disclaimer, the term of this patent is extended or adjusted under 35 U.S.C. 154(b) by 0 days.

(21) Appl. No.: 16/455,850

(22) Filed: Jun. 28, 2019

(65) Prior Publication Data

US 2020/0405392 A1    Dec. 31, 2020

(51) Int. Cl.
*G06T 15/00* (2011.01)
*A61B 34/10* (2016.01)
*G06T 17/20* (2006.01)
*A61B 17/86* (2006.01)

(52) U.S. Cl.
CPC .............. *A61B 34/10* (2016.02); *G06T 15/00* (2013.01); *G06T 17/205* (2013.01); *A61B 17/86* (2013.01); *A61B 2034/102* (2016.02); *G06T 2210/41* (2013.01)

(58) Field of Classification Search
CPC .................................................... G06T 15/00
USPC ....................................................... 345/419
See application file for complete search history.

(56) References Cited

U.S. PATENT DOCUMENTS

| | | | | |
|---|---|---|---|---|
| 2008/0261165 A1* | 10/2008 | Steingart | ............ | A61C 13/0004 433/24 |
| 2008/0319448 A1* | 12/2008 | Lavallee | ................ | G16H 50/50 606/102 |
| 2009/0316966 A1* | 12/2009 | Marshall | ............. | A61B 6/5217 382/128 |
| 2012/0022843 A1* | 1/2012 | Ionasec | ................... | G06T 13/20 703/9 |
| 2013/0211531 A1* | 8/2013 | Steines | ................. | A61F 2/3859 623/20.35 |
| 2015/0112659 A1* | 4/2015 | Mortier | ................... | G06T 17/20 703/11 |
| 2015/0202024 A1* | 7/2015 | Fisker | ................ | A61C 13/0019 433/213 |

(Continued)

*Primary Examiner* — David T Welch
(74) *Attorney, Agent, or Firm* — Alan D. Kamrath; Karin L. Williams; Mayer & Williams PC

(57) ABSTRACT

An implant surface mapping and unwrapping method provided by the present invention selects or defines a mesh implant geometry, and places and rotates it in a specific spatial position according to a mesh. Vertex space coordinates, which are interpolated in medical images such as computed tomography, magnetic resonance imaging, or ultrasound to calculate the gray scale values of these spatial coordinate points, and map them on the surface of the implant. In addition, the implant is irregular. The surface can be further unwrapped through the planar image to help understand its contact with the anatomy. If the medical image is pre-converted to other anatomical, physiological, pathological, and functional parameters, the mapping and unwrapping results will also be displayed with these parameters. Learn more about the relationship between implants and these parameters.

6 Claims, 6 Drawing Sheets

(56) References Cited

U.S. PATENT DOCUMENTS

| | | | |
|---|---|---|---|
| 2015/0230874 A1* | 8/2015 | Musuvathy | A61B 34/10 703/1 |
| 2015/0248538 A1* | 9/2015 | Van Lierde | G06F 17/10 703/2 |
| 2015/0324114 A1* | 11/2015 | Hurley | G16H 50/20 715/850 |
| 2017/0103569 A1* | 4/2017 | Wu | A61B 5/0088 |
| 2017/0323443 A1* | 11/2017 | Dhruwdas | G06T 7/0012 |
| 2018/0168740 A1* | 6/2018 | Ryan | A61B 34/10 |
| 2018/0311035 A1* | 11/2018 | Hirsch | A61B 34/10 |
| 2018/0360609 A1* | 12/2018 | Steines | A61F 2/30 |
| 2019/0321193 A1* | 10/2019 | Casey | A61B 17/7035 |

\* cited by examiner

IMPLANT SURFACE MAPPING AND UNWRAPPING METHOD

BACKGROUND OF THE INVENTION

1. Field of the Invention

The present invention relates to a mapping and unwrapping method, and more particularly to an implant surface mapping and unwrapping method that can generate mesh information with medical information on the surface of the implant.

2. Description of Related Art

In order to improve the accuracy of various types of surgery, surgical navigation systems have been widely used in clinical medicine, while the common surgical navigation systems still mainly present two-dimensional tomographic images. The two-dimensional tomographic images are difficult to cover the stereoscopic information of the complete spatial relationship between the implant and the subject. Therefore, in order to understand more clearly the state and relationship of the complete implant implanted in the three-dimensional structure of the tissue, the surgeon must guide the surgical navigation system to generate tomographic images at different positions. It not only adds complexity and is time consuming, it is also more likely to result in reduced accuracy, and even if fault images of various locations are evaluated, there are still some omissions. In addition, these images provide only basic anatomical information and do not provide additional physiological information to assist with surgical procedures. Furthermore, after the implant is implanted in the subject, it is often necessary to assess the degree of integration with the surrounding tissue and bone to track its efficacy and the safety of the subject. However, most of this process requires two-dimensional tomographic images to be viewed one by one, and this lacks the means to comprehensively examine the degree of integration.

On the other hand, considering the current high cost of a surgical navigation system and the problem of missing blind spots, surgical guide technology has been developed in recent years. The surgical guide is a kind of surgical means that can help the surgeon to cut or implant more accurately. The auxiliary guide plate is mainly designed only with the anatomical appearance of the bones and organs, and it is impossible to evaluate the internal or surrounding information of the surgical site of the subject. To overcome the shortcomings, the present invention tends to provide an implant surface mapping and unwrapping method to mitigate or obviate the aforementioned problem.

SUMMARY OF THE INVENTION

The main objective of the invention is to provide an implant surface mapping and unwrapping method that can generate mesh information with medical information on the surface of the implant.

The implant surface mapping and unwrapping method provided by the present invention selects or defines a mesh implant geometry, and places and rotates it in a specific spatial position according to a mesh. Vertex space coordinates, which are interpolated in medical images such as computed tomography, magnetic resonance imaging, or ultrasound to calculate the gray scale values of these spatial coordinate points, and map them on the surface of the implant. In addition, the implant is irregular. The surface can be further unwrapped through the planar image to help understand its contact with the anatomy.

An implant surface mapping and unwrapping method which can be executed by a computer that has calculus and storage capabilities includes: reading a computer file of an implant by the computer to generate a mesh on an outer surface of the implant; setting the mesh in a coordinate space by the computer and defining spatial feature of mesh units of the mesh in the coordinate space; reading a file of medical information by the computer and calculating the medical value of each mesh unit of the mesh when the medical information is overlapped with the coordinate space; mapping the medical information to the coordinate that is corresponding to the mesh unit; and expanding the mesh into a two-dimensional image by the computer.

If the medical image is pre-converted to other anatomical, physiological, pathological, and functional parameters, the mapping and unwrapping results will also be displayed with these parameters, learning more about the relationship between implants and these parameters. From the above description, the advantages and features of the present invention include:

First, the present invention shows the contact situation of the implant with the human body in a specific space placement position, and according to the medical image information used, the contact information of the anatomical, physiological, pathological or functional parameters can be used to help the surgical guide plate design and preoperative planning and selection of surgical execution methods and integration of implants and tissues, implant mapping and/or deployment methods of medical imaging information can effectively overcome the problems of current surgical navigation systems, and are widely used in surgical puncture and implantation. Surgical navigation such as entry, drilling and slicing can also be applied to interstitial therapy and brachytherapy. The applicable scope includes surgical navigation, preoperative planning, guide design, implant integration assessment. In the radionuclide position assessment of interstitial therapy and brachytherapy, the prior art of the surgical navigation system is inferior to the function proposed by the present invention, and thus is highly competitive.

Second, in addition to being directly integrated with the surgical navigation system, the present invention can also be linked with an imaging device, a stereotactic system, a surgical robot, a guide plate design, a surgical planning software, an insertion and advanced treatment planning system, and an integrated manufacturer.

Third, the implant surface mapping and unwrapping method provided by the invention selects or defines the mesh implant geometry, and places and rotates it in a specific spatial position, according to the mesh vertex space coordinates, in interpolating the gray scale values of the spatial coordinate points in a medical image such as computed tomography, magnetic resonance imaging or ultrasound, and mapping on the surface of the implant. In addition, the irregular surface of the implant can further spread through the planar image to help to understand the contact with the anatomy, if the medical image is pre-converted to other anatomical, physiological, pathological, and functional parameters, the mapping and unwrapping results will also be displayed with these parameters to further understand the relationship between the implant and these parameters. Other objects, advantages and novel features of the invention will become more apparent from the following detailed description when taken in conjunction with the accompanying drawings.

BRIEF DESCRIPTION OF THE DRAWINGS

FIG. 1b is a perspective of a mesh with physiological information of the implant in FIG. 1a;

DETAILED DESCRIPTION OF PREFERRED EMBODIMENT

Figure 1A:
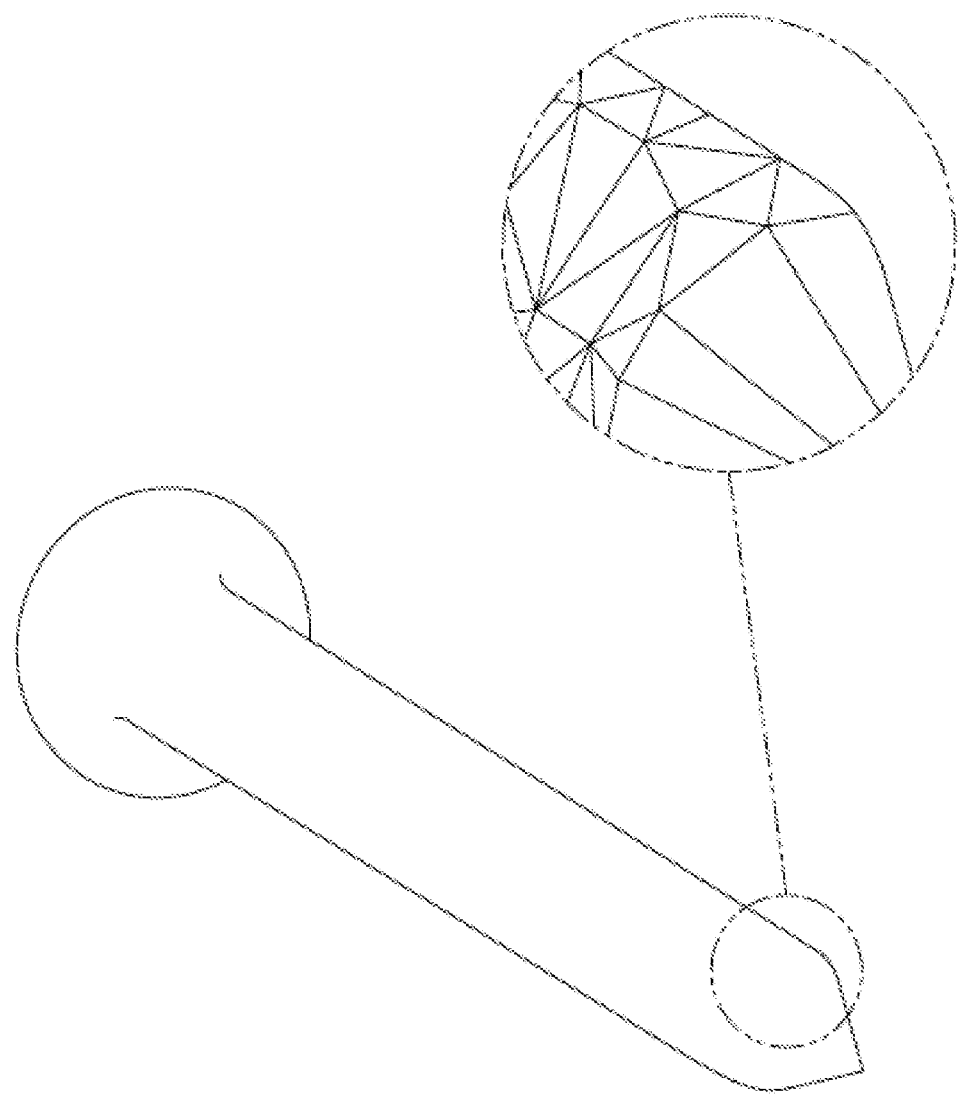
FIG. 1a is a perspective view of an implant with diagram showing mapping of interpolation information to a mesh of the implant in accordance with the present invention.

With reference to FIGS. 1a, 1b, 2, 3a, 3b, and 4, the present invention provides an implant surface mapping and unwrapping method, which it can be executed by calculation of a computer, and the computer has functions of calculation, loading data and data storage. The implant surface mapping and unwrapping method can also called the implant surface mapping and mapping unwrapping (or unfolding) method which the steps of the present invention are as follows:

First step, generate mesh data for the implant:

The implant may be an implant, a guide, or the like that may be placed into a living body for different medical needs, and the implant may be a bone nail, a prosthesis, a stent, or the like. The implant has a surface appearance type according to different medical requirements, and is not limited to a curved surface type, a spiral type, a sheet type, and the like. The appearance of the implant determines a mesh (MESH) of an outer surface of the implant through stereoscopic scanning, three-dimensional modeling, etc. For example, FIG. 1a shows the implementation of a mesh distribution of a bone nail of the present invention.

Second step, define mesh space features:

The mesh in the first step is set in a coordinate space, and one or more feature points of the mesh are obtained from a spatial feature in the coordinate space. The feature points may include the appearance vertices, side walls, bottom points, etc. of the mesh corresponding to the implant. The feature point may be an intersection or a limit value of each mesh unit of the mesh of the implant in the coordinate space, thereby defining spatial features of the plurality of mesh units of the implant in the coordinate space, the spatial features may be coordinate values, vectors, faces, and the like.

Third step, corresponding medical information to the coordinate space and calculating the medical values of the feature points:

A medical information correspondingly is placed in the coordinate space, wherein the medical information includes at least one biological image, and information selected from the group consisting of a physiological parameter, a pathological parameter, and a functional parameter. The biological image may be a computed tomography image (CT), a magnetic resonance image (MR), an ultrasound images, an X-ray stereo model image, or the like. The biological image, the physiological parameter, the pathological parameter, and the content of the functional parameter respectively correspond to the spatial feature of the coordinate space.

The coordinates of each feature point are calculated corresponding to the biological image, the physiological parameter, the pathological parameter, and/or the value or information of the functional parameter (the medical information), so that the feature point corresponds to the medical information. Among them, the medical information can include the following:

Taking a bone screw as an example, the medical information may be a bone area fraction, a plane bone density, etc. corresponding to some of the feature points/mesh units.

Taking a guiding tube of angiography as an example, the medical information may correspond to a cross-sectional flow rate or a flow rate of some of the feature points/mesh units.

Taking a chest tube as an example, the medical information may be a gas-bearing area fraction and a plane gas density corresponding to some of the feature points/mesh units.

Taking an advanced treatment as an example, the medical information may be a tissue image corresponding to a corresponding feature point/mesh unit of the implant contact tissue.

Taking an artificial knee joint as an example, the implant is an artificial knee joint, and the medical information is that the feature point/mesh unit corresponding to the surface of the artificial knee joint can correspond to some of the feature points/mesh unit and femur integration rate data.

The bone volume/total volume (BV/TV) and the volumetric bone mineral density (vBMD) may be obtained by further converting a tomographic image (CT image). Since the CT value is calculated from the attenuation coefficient, and the attenuation coefficient represents the attenuation ability of the tissue for X-ray, it is proportional to the physical density of the tissue, as most bone density measurement techniques simplify the bone into cortical bone and bone marrow. The cortical bone-bone marrow equivalent prosthesis of known combination ratio can be used as a reference standard, and the CT value can be directly converted into a two-compartment model (TCM) by quantitative CT or Shih et al. Bone volume fraction (BV/TV) and volumetric bone mineral density (vBMD), in which CT value is converted to bone physiological parameters, the bone volume can be calculated using TCM proposed by Shih et al. The fractional or volumetric bone density, which requires only a single standard sample as a reference, can be converted to bone physiological parameters by the above steps. In addition, general scientific research or clinical practices mostly consider human bones as the main two tissues. The composition is bone tissue and bone marrow, respectively, like quantitative CT (quantitative CT), using materials with similar photon attenuation characteristics to the two tissues, evenly mixed in different proportions (the bone tissue can be dipotassium hydrogen phosphate or hydroxyapatite, and the bone marrow tissue can be distilled water or secondary water) to produce an equivalent bone material that can simulate different bone density, because the material ratio of the implant is known. The CT value can also be calculated directly after CT scan. Therefore, it is only necessary to compare and interpolate the CT value on the clinical CT image with the CT values of these calibration prostheses, and then the CT value can be converted to a bone density equivalent to the bone material.

Figure 1B:
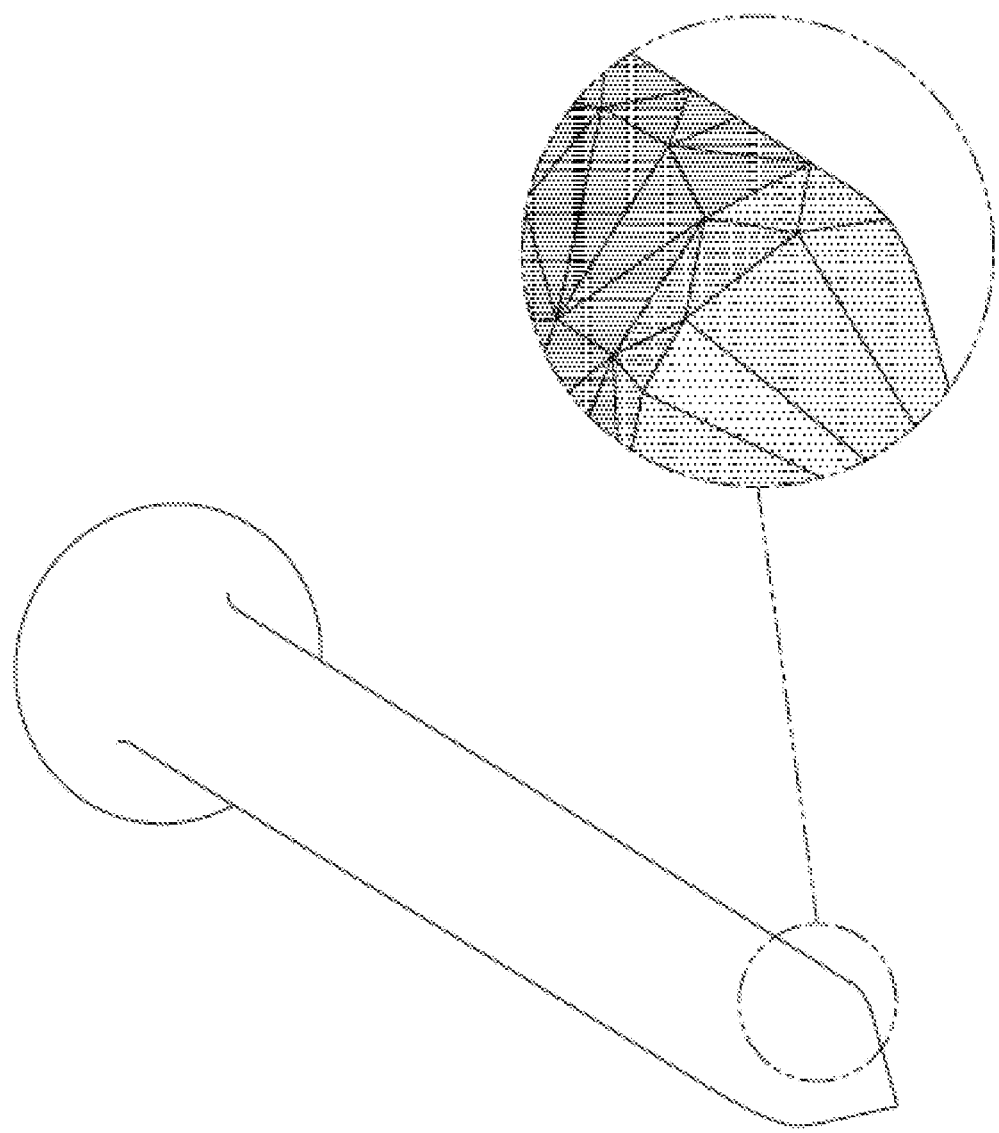
Figure 4:
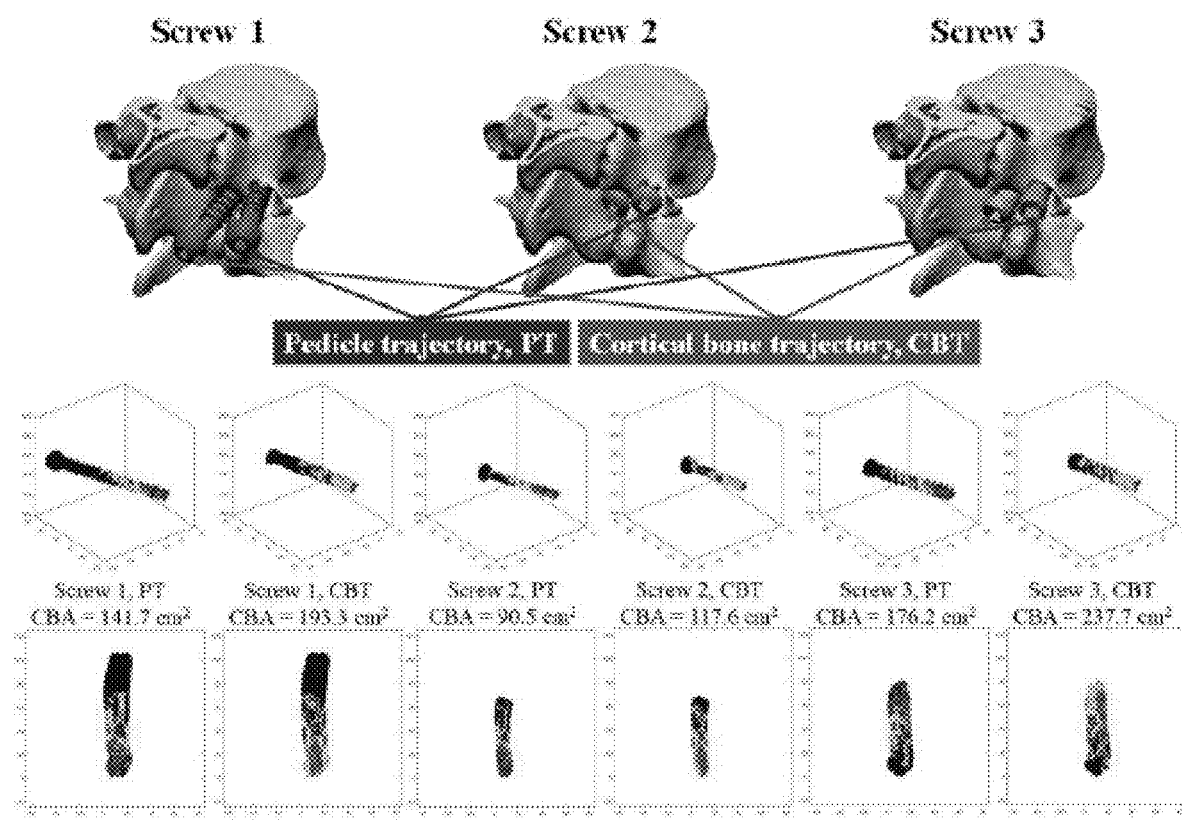
FIG. 4 is a schematic view showing the unwrapped and wrapped physiological information images of the bone nail implanted at different positions in accordance with the present invention.

Fourth step, mapping medical information to mesh units/feature points:

Mapping the result of the vertex interpolation to the surface of the mesh such that each mesh unit correspondingly contains medical information. With reference to FIGS. 1a and 1b, which are examples of interpolating medical information in the mesh. The implant is a screw, and the biological image placed on the human body is as shown in FIG. 1a, and the foregoing mapping method is adopted. The medical information (this embodiment is the bone volume fraction) is mapped to the surface of the mesh. With reference to FIG. 4, it shows the screw surface contact bone area (CBA) of the three screws in the pedicle trajectory (PT) and the cortical bone trajectory (CBT). The three-dimensional model diagram shows the direction of the spine and screw implant. The results of the bone area fraction are plotted on the front and back surfaces of the screw.

Wherein, in the foregoing third step and fourth step, the coordinates of the three-dimensional medical information are obtained, and the coordinates of the three-dimensional medical information should be directly mapped to the plane of the mesh. Since the correspondence between the grid and the three-dimensional medical information is not necessarily one-to-one. A mesh unit may correspond to one of the more medical information voxels. The gray level of the voxel is the signal intensity of the coordinate point. Therefore, the tomographic image can be regarded as a three-dimensional rectangular mesh data distribution.

The aforementioned implant, such as a screw mesh, is also formed by the spatial features (vertex) described by a plurality of spatial coordinates, so that when the implant mesh is placed at the specific position, such as a screw according to the tomographic image placed on the stud path of common spinal fusion surgery, so that the spatial coordinate range of the image voxel and the vertices of the screw mesh will overlap. The image signal intensity at the vertex space position can be obtained by interpolating the signal intensity of the surrounding voxels, and then the signal intensity of the three vertices constituting the mesh face is averaged and then drawn on the mesh face. This completes the surface texture rendering of the mesh, enabling the mesh surface to carry specific information, solving the problem of mesh and 3D medical information.

Using the aforementioned inner fork and averaging calculations, each mesh unit can contain a variety of medical information, such as water molecule signals of MR images, CT values of CT images, or volumetric bone density obtained by conversion. With the mesh expanding, the implant and tissue contact can be displayed on a two-dimensional planar mesh, which will greatly simplify the implant path, implant location selection and safety judgment.

In addition, under the depiction of the volumetric bone density, the bone contact of the screw can be better understood, and the stability of the implantation path can be evaluated.

In order to ensure the correctness of the interpolation data, the present invention uses a tricubic interpolation calculation, which can be achieved through the Catmull-Rom interpolating curves. The formula of the one-dimensional form is as follows:

$$C(u) = [u^3 \ u^2 \ u \ 1] \begin{bmatrix} -0.5 & 1.5 & -1.5 & 0.5 \\ 1.0 & -2.5 & 2.0 & -0.5 \\ -0.5 & 0 & 0.5 & 0 \\ 0 & 1 & 0 & 0 \end{bmatrix} \begin{bmatrix} p_{i-1} \\ p_i \\ p_{i+1} \\ p_{i+2} \end{bmatrix}$$

Among them, C(u) is the interpolation result, and $p_{i-1}$, $p_i$, $p_{i+1}$, and $p_{i+2}$ are four consecutive data points. In three dimensions, the tricubic interpolation is calculated in the same direction for each of the three directions. First, 16 interpolations are performed using 64 data points in the x direction, and then the 16 data points interpolated in the x direction are interpolated four times in the y direction, and finally the interpolation is performed by the four data points in the z direction, and the result of the triple interpolation can be obtained. In the FIG. 4, compare the difference in contact bone mass of the three screws at the same path and depth of implantation to understand the relationship between thread design and contact bone mass.

Fifth step, expand the mesh to form a 2D image:

The suture between two adjacent mesh units of the mesh is selected, and the mesh is unwrapped into a two-dimensional image to more directly observe medical information of the contact portion between the implant and the living body.

With reference to FIG. 1b, which is a development view of the medical information mapping in the mesh of the pedicle and cortical bone of the above-mentioned FIG. 1a. The design of the mesh not only can obtain the relationship between the implant and the human body contact be obtained, but also all the possible effects on the human body during the operation can be judged. At the same time, the stability of the implant in the human body can be directly analyzed. Appropriate, and the mesh can increase the speed of the navigation system and improve the accuracy of the surgery.

However, the implant has different three-dimensional structures because of functional requirements, but these three-dimensional structures are not conducive to the observation of these information (as shown in FIG. 1b), and the structure needs to be manually flipped to observe each aspect. It must be developed through this step to make it easier to observe.

Figure 2:
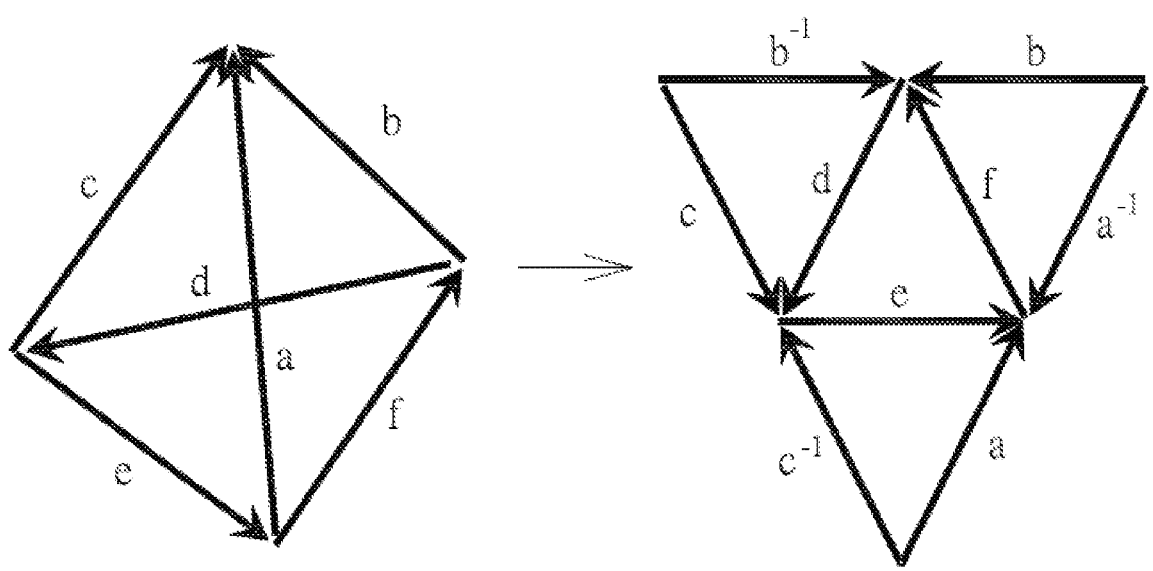
FIG. 2 is a schematic diagram of a mesh leveling calculation in accordance with the present invention.
Figure 3A:
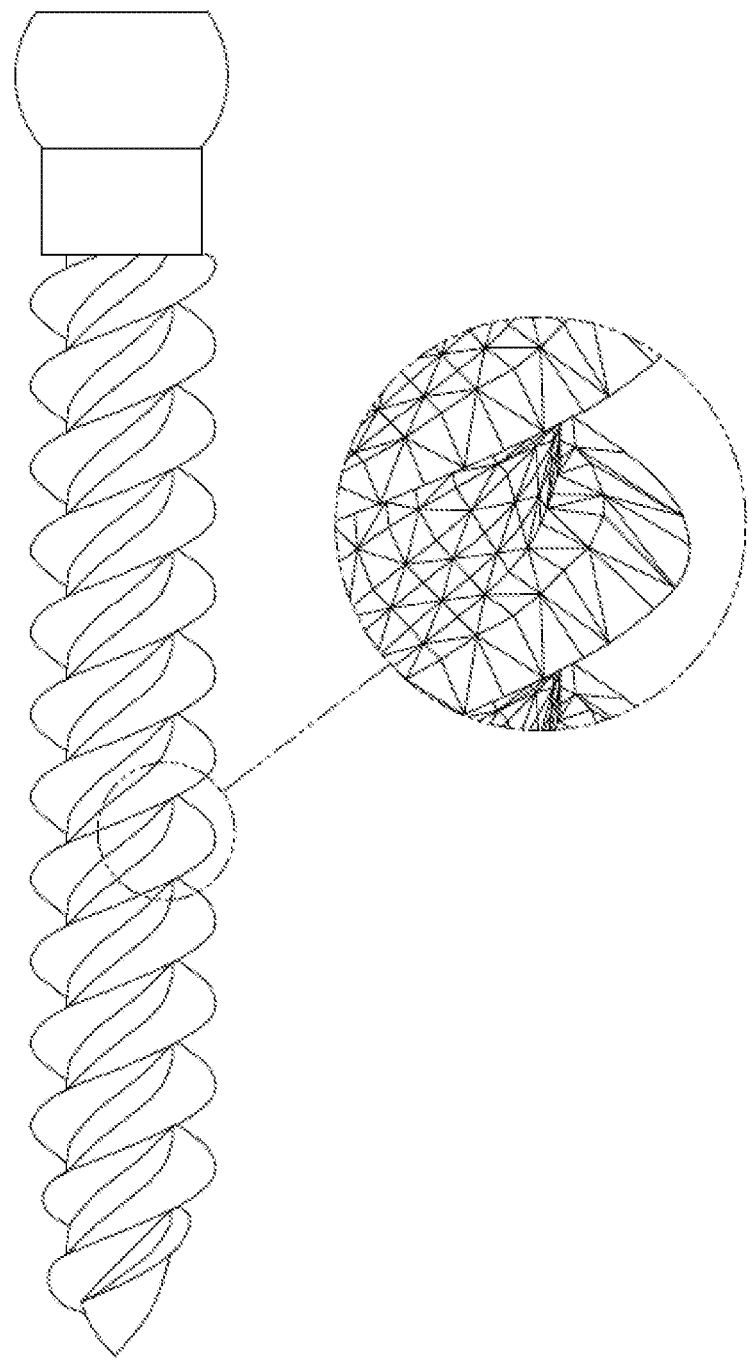
FIG. 3a is a perspective view of a wrapped mesh of a bone nail in accordance with the present invention.
Figure 3B:
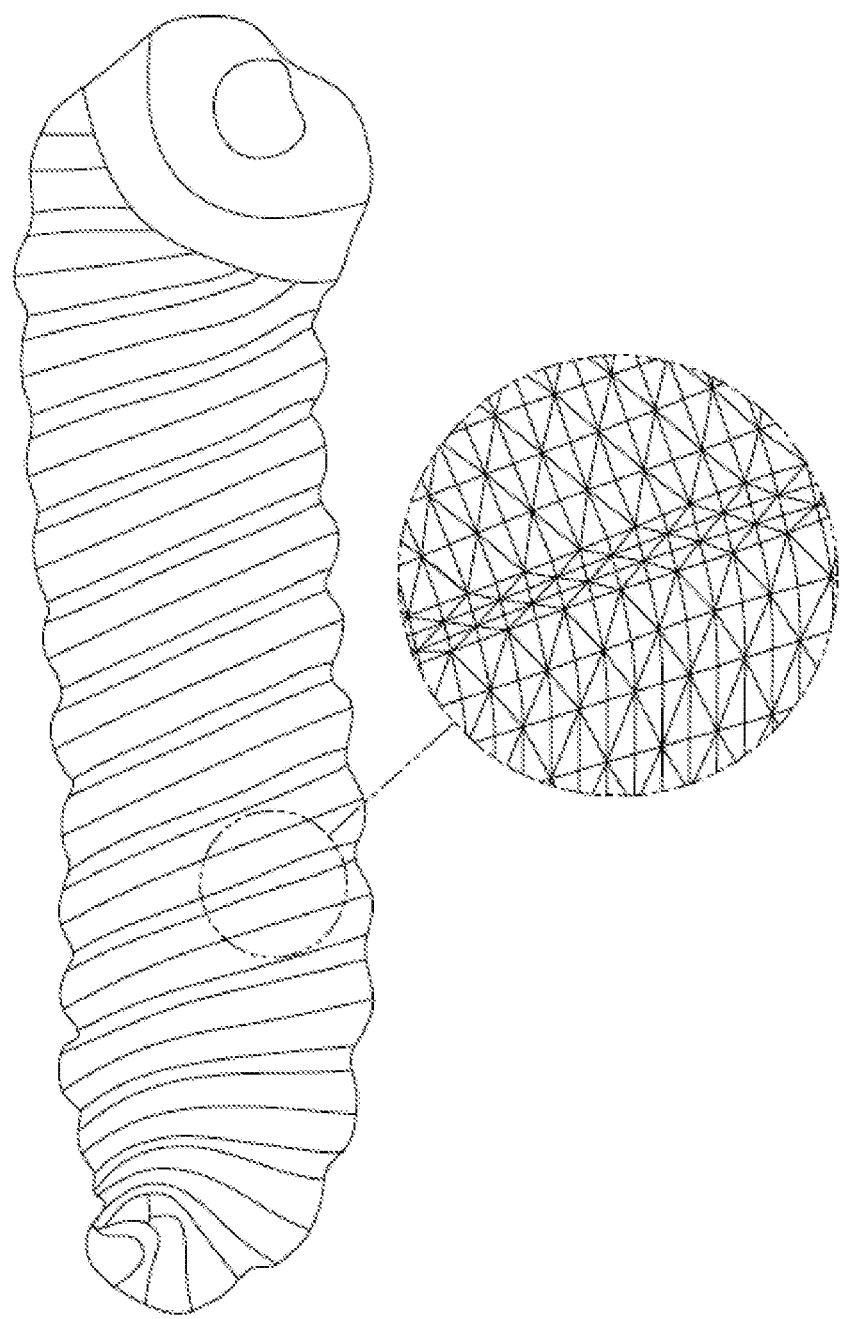
FIG. 3b is a perspective view of an unwrapped mesh of a bone nail in accordance with the present invention.

Referring to FIGS. 2, 3a, and 3b, the preferred embodiment of this step can be spread out into a two-dimensional mesh distribution information by a topological surgery mesh. In topological surgery, first through the manual or automatically defined mesh gap (seem), then in a predefined order, such as counterclockwise, along the gap to encode the boundaries of the three-dimensional mesh, and finally according to the original dimensions of each boundary and its connected relationship, all triangular meshes are laid flat in the order of the two dimensions. The right side of FIG. 2 shows the flattening result after dividing the mesh along the three boundaries of a, b, c, so that the complex three-dimensional mesh structure is changed to a flat mesh, which can effectively improve the visibility of the data. Accordingly, comparing FIGS. 3a and 3b, in this embodiment, the longest mesh path of the screw is a slit, the screw is flattened by the foregoing method, and the wrapped screw grid (FIG. 3a) forms an unwrapped screw grid (FIG. 3b).

It can be seen from the foregoing description that the present invention utilizes a mesh and a special mesh surface texture rendering algorithm to quickly and accurately confirm the positional relationship and physical contact relationship between the implant and the human tissue. In this way, the difference between the actual and simulated implants can be known through the second photography, and then the design of the implant is adjusted. The application of the present invention is diversified, and the brackets with complex surfaces such as hollow appearance can be projected, and the medical information of different resolutions is integrated, which can be used for redesigning and adjusting the implants and adjust the characteristics of the local material to enhance the bonding relationship with the tissue and cell growth.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An implant surface mapping and unwrapping method comprising:
   generating mesh data for an implant by:
   preparing an implant with an outer surface; and
   determining a mesh of the outer surface of the implant;
   defining mesh space features by:
   setting the mesh in a coordinate space; and
   defining a spatial feature of at least one feature point or mesh unit of the mesh in the coordinate space, wherein the spatial feature is a coordinate value, vector, or face which corresponds to a feature point of the mesh, and the feature point is an appearance vertex, side wall or a bottom point;
   calculating medical values of the feature point or the mesh unit and placing medical information to the coordinate space, wherein the medical information comprises a biological image and information selected from a group consisting of a physiological parameter, a pathological parameter, and a functional parameter;
   mapping medical information to the feature point or the mesh unit; and
   expanding the mesh into a two-dimensional image, wherein a mesh gap of the mesh of the implant is defined, and through the defined mesh gap in a counterclockwise order, the boundaries of an three-dimensional mesh along the defined mesh gap in the order of two dimensions is encoded and defined, and finally, according to the original dimensions of each boundary and its connected relationship, all triangular meshes are laid flat in the order of the two dimensions.

2. The implant surface mapping and unwrapping method as claimed in claim 1, wherein the medical information comprises one of bone area fraction, a plane bone density, a cross-sectional flow rate or a flow rate, gas-bearing area fraction, a plane gas density, a tissue image, and a femur integration rate data.

3. The implant surface mapping and unwrapping method as claimed in claim 1, wherein in the step of calculating the medical values of the feature point or the mesh unit and placing the medical information to the coordinate space, an interpolation and averaging method is used, and values of adjacent medical information coordinates are averaged to correspond to specific mesh units of the associated mesh.

4. The implant surface mapping and unwrapping method as claimed in claim 2, wherein in the step of calculating the medical values of the feature point or the mesh unit and placing the medical information to the coordinate space, an interpolation and averaging method is used, and values of adjacent medical information coordinates are averaged to correspond to specific mesh units of the associated mesh.

5. An implant surface mapping and unwrapping method which can be executed by a computer that has calculus and storage capabilities, and comprising:
   reading a computer file of an implant by the computer to generate a mesh of an outer surface of the implant;
   setting the mesh in a coordinate space by the computer and defining a spatial feature of mesh units of the mesh in the coordinate space, wherein the spatial feature is a coordinate value, vector, or face which corresponds to a feature point of the mesh, and the feature point is an appearance vertex, side wall or a bottom point;
   reading a file of medical information by the computer and calculating a medical value of each mesh unit of the mesh when the medical information is overlapped with the coordinate space, wherein the medical information comprises a biological image and information selected from a group consisting of a physiological parameter, a pathological parameter, and a functional parameter;
   mapping the medical information to the coordinate that is corresponding to each mesh unit; and
   expanding the mesh into a two-dimensional image by the computer, wherein a mesh gap of the mesh of the implant is defined, and through the defined mesh gap in a counterclockwise order, the boundaries of an three-dimensional mesh along the defined mesh gap in the order of two dimensions is encoded and defined, and finally, according to the original dimensions of each boundary and its connected relationship, all triangular meshes are laid flat in the order of the two dimensions.

6. The implant surface mapping and unwrapping method as claimed in claim 5, wherein the computer takes medical information placing to a partial overlap of the coordinates of a specific mesh unit, and maps the medical information of the specific mesh unit by taking an average value after interpolation.

\* \* \* \* \*